United States Patent [19]

Hochstein

[11] 4,206,282

[45] Jun. 3, 1980

[54] HYPERTONIC CULTURE MEDIA

[75] Inventor: Francis A. Hochstein, New London, Conn.

[73] Assignee: Pfizer Inc., New York, N.Y.

[21] Appl. No.: 828,946

[22] Filed: Aug. 29, 1977

[51] Int. Cl.$^2$ .............................................. C12Q 1/04
[52] U.S. Cl. ...................................... 435/34; 435/36; 435/38; 435/253
[58] Field of Search ................. 195/99, 100, 101, 102; 435/34, 36, 38, 253

[56] References Cited

U.S. PATENT DOCUMENTS

| | | | |
|---|---|---|---|
| 3,704,204 | 11/1972 | Heck et al. | 195/100 |
| 3,827,942 | 8/1974 | Janik | 195/100 |
| 3,902,969 | 9/1975 | Gold | 195/100 X |
| 3,928,139 | 12/1975 | Dorn | 195/103 SM |
| 4,061,537 | 12/1977 | Seiler et al. | 195/100 X |

OTHER PUBLICATIONS

The Handbook of Food Additives, The Chemical Rubber Company, 1968, p. 459.

*Primary Examiner*—Robert J. Warden
*Attorney, Agent, or Firm*—Connolly and Hutz

[57] ABSTRACT

Improved hypertonic culture media, employing mannitol, erythritol or sorbitol in place of sucrose to provide high osmolarity, are described for the detection and growth of microorganisms in body fluids, particularly of bacteria in blood specimens.

3 Claims, No Drawings

HYPERTONIC CULTURE MEDIA

BACKGROUND OF THE INVENTION

The use of hyperosmolar media for the support of the growth of protoplasts, spheroplasts and L-forms of bacteria is well established (L. B. Guze, Microbial Protoplasts, Spheroplasts and L-forms, Williams and Wilkins, Baltimore, Md., 1968). The extensive application of hyperosmolar media to the detection of bacteremia is more recent: Am. J. Med. Tech., 35, 702–5 (1969); Microbiol., 19, 281–2 (1970); Am. J. Clin. Path., 57, 220–7 (1972); Abst. Ann. Meeting, Am. Soc. Microbiol., No. M48, 81 (1973).

Virtually all studies of clinical samples have utilized media in which sucrose is used to elevate the osmotic strength to 600 milliosmolar or higher. Alternative solutes to sucrose have had very limited study. Ionizable salts, e.g., sodium and potassium chloride, are of limited value and are not favored (Antonie van Leeuwenhoek, 36, 21–31 (1970). Glycerol penetrates microbial cell walls and is not useful (J. Gen. Microbiol., 82, 125–42 (1974).

Although the recovery rate of pathogenic bacteria from sucrose fortified media is satisfactory, sucrose has disadvantages in blood culture. At the 10% or higher concentrations used, sucrose media are more dense and more viscous than the base media. Settling of erythrocytes is therefore slower and less complete, and the visual detection of modest microbial growth can be difficult. After incubation for 24 hours or more, sucrose media also show hemolysis of the erythrocytes, and the resultant dark fluids are too opaque for the detection of modest microbial growth. Subculturing of these media is therefore too often necessary to ensure that growth is detected.

A medium which retains the growth promoting properties of high osmolarity sucrose media, free of these disadvantages, would provide the clinical microbiologist a tool that could allow more facile and more rapid detection of bacteremia.

SUMMARY OF THE INVENTION

This invention is concerned with hypertonic culture media, particularly for the detection and growth of bacteria in blood specimens, in which mannitol, erythritol or sorbitol is employed to impart the desired hyperosmolarity. It has been found that the viscosity of culture broth with 5% sorbitol, and by analogy mannitol and erythritol, is significantly lower than that of the broth with 10% sucrose. This results in more complete settling of the erythrocytes in the blood sample. Furthermore, the hemolysis of freshly drawn human blood in culture broth established experimentally with 5% sorbitol, mannitol or erythritol is markedly less after 1–14 days incubation at 35° C. than that of the same sample in a 10% sucrose medium. These factors substantially facilitate the visual examination of cultured blood samples for the detection of bacterial growth.

DETAILED DESCRIPTION OF THE INVENTION

Although the invention will be described herein in particular with reference to hypertonic media and the preparation thereof for the use in culturing blood specimens for the detection and growth of bacteria therein, since this is at present the most practical use of the invention, as those skilled in the art will readily appreciate, the invention can be used for culturing body fluids in general such as e.g. cerebrospinal fluid and urine for the detection and growth of microorganisms in general therein.

Polyhydric alcohols, of which mannitol, erythritol and sorbitol are examples, have not been the subject of previous studies for the replacement of sucrose in hypertonic culture media for the detection of bacteremia.

A variety of culture media are available for the detection and growth of bacteria in blood specimens. The cultural and growth requirements of many of these delicate and fastidious organisms may be favored by one culture medium over others. In general, blood samples are preferably cultured in hypertonic media in a carbon dioxide atmosphere, aerobic and anaerobic environment and with the use of an anticoagulant (preferably sodium polyanethol sulfonate).

Osmolarity is defined as the molarity of an ideal solution of a non-dissociating substance that exerts the same osmotic pressure as the solution being considered (Dictionary of Scientific and Technical Terms (McGraw-Hill, 1974). Blood plasma has an osmolarity (milliosmoles/liter) of about 290. In order to prevent the undesirable hemolysis of erythrocyes in the clinical blood sample, the culture medium is made hypertonic (osmolarity $>$ 290). The concentration of mannitol, erythritol or preferably sorbitol employed may extend over a fairly wide range. Culture broths may be made hypertonic according to the invention by addition of sorbitol at a concentration of about 3.5 to about 9% w/v, perferably about 5 to about 9% w/v, more preferably about 6% w/v, or iso-osmolar amounts of mannitol or erythritol. The commonly used osmolarity range for hypertonic media is about 600–900 milliosmoles.

Some comparative results which are obtained by replacing prior art sucrose with the invention sorbitol in hypertonic culture media are as follows:

1. Sorbitol (M.W. 182) at a concentration of 5.35% w/v provides a medium of the same osmolarity, about 650 milliosmolar, to one containing 10% sucrose (M.W. 343).

2. The viscosity and density of a culture broth with 5% sorbitol is significantly lower than that of the same broth with 10% sucrose. This results in more complete settling of erythrocytes (density 1.098 at 290 milliosmolar) and other formed elements of blood. The density and viscosity of mannitol and erythritol iso-osmolar to 10% sucrose are also lower.

3. The hemolysis of freshly drawn human blood in culture broth with 5% sorbitol and also of 5% mannitol and 4% erythritol is markedly less after 1–14 days incubation at 35° C. than that of the same sample in a 10% sucrose medium.

4. The number of microorganisms which metabolize sorbitol is about the same as that metabolizing sucrose.

5. Sorbitol, mannitol and erythritol are no more inhibitory to microorganisms than sucrose or other sugars or salts at nutrient concentrations.

6. Sorbitol, mannitol and erythritol are as chemically stale as sucrose.

7. The cost of sorbitol at 5% concentration approximates that of sucrose at 10% concentration.

Mannitol, erythritol or preferably sorbitol can be advantageously employed in hypertonic culture media as a replacement for sucrose for the culturing of blood samples for the detection and growth of protoplasts, spheroplasts and L-forms and antibiotic weakened strains of bacteria. Hypertonic culture media with sorbitol are suitable for the detection and growth of a variety of pathogenic bacteria such as *Staphylococcus aureus, Streptococcus pyogenes, Diplococcus pneumoniae, Escherichia coli, Klebsiella pneumoniae, Proteus mirabilis, Pseudomonas aeruginosa, Hemophilus influenzae, Brucella suis, Brucella abortus, Clostridium novyi, Bacteroides vulgatus* and other bacteria that may be associated with bacteremia.

EXAMPLE I

The following sterile aqueous media are prepared:

| Composition | Approximate Grams/Liter of Aqueous Solution |
|---|---|
| A. Brucella Broth | |
| Pancreatic Digest of Casein | 15.0 |
| Enzymatic Digest of Animal Tissue | 4.0 |
| Yeast Extract | 2.0 |
| Sodium Chloride | 5.0 |
| Dextrose | 0.9 |
| Sodium Citrate | 1.0 |
| Sodium Bisulfite | 0.1 |
| Sodium Polyanethol Sulfonate | 0.5 |
| Sorbitol | 60.0 |
| Approximate pH 7.0 | |
| B. Columbia Broth | |
| Pancreatic Digest of Casein | 10.0 |
| Enzymatic Digest of Animal Tissue | 5.0 |
| Yeast Extract | 5.0 |
| Pork Heart Digest | 3.0 |
| Sodium Chloride | 5.0 |
| Dextrose | 2.5 |
| L-Cysteine HCl | 0.1 |
| Magnesium Sulfate . 7H$_2$O | 0.1 |
| Ferrous Sulfate . 7H$_2$O | 0.02 |
| Sodium Carbonate | 0.6 |
| Tris Base | 0.83 |
| Tris HCl | 2.86 |
| Sodium Citrate | 0.1 |
| Sodium Polyanethol Sulfonate | 0.5 |
| Sorbitol | 60 |
| Approximate pH 7.4 | |
| C. Brain Heart Infusion Broth | |
| Brain Heart Infusion | 15.0 |
| Enzymatic Digest of Animal Tissue | 10.0 |
| Yeast Extract | 2.5 |
| Dextrose | 2.25 |
| Sodium Chloride | 5.0 |
| Sodium Citrate | 1.0 |
| Disodium Phosphate | 1.3 |
| Sodium Polyanethol Sulfonate | 0.5 |
| Sorbitol | 35 |
| Approximate pH 7.4 | |
| D. Tryptic Soy Broth | |
| Tryptic Digest of Casein | 5.0 |
| Pancreatic Digest of Casein | 11.0 |
| Papaic Digest of Soybean Meal | 3.0 |
| Dextrose | 2.5 |
| Dipotassium Phosphate | 2.5 |
| Sodium Chloride | 5.0 |
| Sodium Citrate | 1.0 |
| Sodium Polyanethol Sulfonate | 0.5 |
| Sorbitol | 90 |
| Approximate pH 7.3 | |
| E. Thioglycollate Medium w/o Indicator | |
| Tryptic Digest of Casein | 17.0 |
| Papaic Digest of Soybean Meal | 3.0 |
| Yeast Extract | 2.0 |
| Dextrose | 5.0 |
| Sodium Chloride | 2.6 |
| Sodium Thioglycollate | 0.5 |
| L-Cystine | 0.1 |

| Composition | Approximate Grams/Liter of Aqueous Solution |
|---|---|
| Sodium Bisulfite | 0.1 |
| Agar | 0.7 |
| Sodium Polyanethol Sulfonate | 0.5 |
| Sorbitol | 60 |
| Approximate pH 7.0 | |

The sterile media are dispensed into 50 ml and 100 ml bottles. All bottles contain added carbon dioxide equivalent to 120 ml CO$_2$ gas per liter, and vacuum.

Typically, drawn blood (5 ml) is allowed to flow into a 50 ml bottle and 10 ml in a 100 ml bottle. The vacuum in the culture bottle normally provides adequate mixing of the blood and medium. Specimens are incubated at 35° to 37° C. for up to 14 days. Specimens are examined within 24 hours and daily thereafter for up to 14 days for visible signs of growth as indicated by turbidity, decolorization of the blood, hemolysis, colonization of the blood layer or gas production within the culture bottle. Positive samples may be validated by subculture.

EXAMPLE II

Sorbitol in the culture media of Example I may be replaced by iso-osmolar amounts of mannitol or erythritol.

EXAMPLE III

Culture media of Example I containing polyhydric alcohols at different concentrations were compared for osmolarity.

| | Osmolarity |
|---|---|
| Tryptic Soy Broth with 5% sorbitol | 552 |
| Tryptic Soy Broth with 11% sorbitol | 895 |
| Brucella Broth with 5% sorbitol | 632 |
| Brucella Broth with 10% sorbitol | 881 |
| Brucella Broth with 6% mannitol | 659 |
| Brucella Broth with 3.6% erythritol | 644 |
| Columbia Broth with 8% sorbitol | 866 |

EXAMPLE IV

Sterile blood (5 ml) was added to a series of bottles each containing 50 ml of Brucella Broth of Example I containing 5% sorbitol and the same broth containing 10% sucrose. The media were examined daily for 7 days. Care was taken not to disturb the settled red blood cells.

| Day | 5% Sorbitol | 10% Sucrose |
|---|---|---|
| 1 | Slightly turbid | Slightly turbid |
| 2 | Clear | Slightly turbid |
| 3 | Clear | Slightly turbid |
| 4 | Clear | Turbid |
| 5 | Clear | Very turbid |
| 6 | Clear | Very turbid |
| 7 | Slightly turbid | Extremely turbid |

EXAMPLE V

A comparison was made between the properties of Brucella Broth of Example I containing 5% sorbitol and the same broth containing 10% sucrose before the addition of blood sample:

|  | 5% Sorbitol | 10% Sucrose |
| --- | --- | --- |
| Sp. Gravity | 1.028 | 1.048 |
| Viscosity (centipoise units, 23° C.) | 0.99 | 1.04 |
| Settling rate of erythrocytes, mm./hr. | 6.45 | 5.25 |
| Turbidity; O.D. @ 580 mm 11 mm cell @ 24 hours | 0.190 | 0.293 |
| Milliosmoles/liter | 604 | 645 |

EXAMPLE VI

Whole blood (5 ml) was added to 50 ml of the Brucella Broths of Example IV. The rate of red blood cell settling was determined by measuring the height of the supernatant (that portion which visually contains no red blood cells).

|  | Mean Settling Distance (mm) | |
| --- | --- | --- |
| Time (hrs.) | 5% Sorbitol | 10% Sucrose |
| 0 | 0 | 0 |
| 1 | 4 | 3 |
| 2 | 6.5 | 4 |
| 3 | 9 | 6 |
| 4 | 11.5 | 8.5 |
| 5 | 15 | 11 |
| 6 | 19 | 13.5 |
| 7 | 23 | 17 |
| 8 | 27 | 21 |
| 24 | 45 | 43 |

What is claimed is:

1. In the process of preparing a hypertonic bacteriological culture medium, the improvement which comprises employing about 3.5 to about 9% w/v of a polyhydric alcohol selected from the group consisting of mannitol, erythritol and sorbitol as the hypertonic agent.

2. The process of claim 1 wherein said polyhydric alcohol is sorbitol.

3. A hypertonic bacteriological culture medium consisting essentially of a bacterial culture medium and about 3.5 to about 9% w/v of sorbitol as the hypertonic agent.

* * * * *